United States Patent [19]

Stuerzebecher et al.

[11] Patent Number: 5,523,321

[45] Date of Patent: Jun. 4, 1996

[54] PROSTACYCLINS, THEIR ANALOGS OR PROSTAGLANDINS AND THROMBOXANE ANTAGONISTS FOR TREATMENT OF THROMBOTIC AND THROMBOEMBOLIC SYNDROMES

[75] Inventors: Claus-Steffen Stuerzebecher; Werner Witt; Bernd Raduechel; Werner Skuballa; Helmut Vorbrueggen, all of Berlin, Germany

[73] Assignee: Schering Aktiengeselleschaft, Berlin, Germany

[21] Appl. No.: 504,071

[22] Filed: Apr. 2, 1990

Related U.S. Application Data

[63] Continuation of Ser. No. 41,013, Mar. 18, 1987, abandoned, filed as PCT/DE86/00260 published as WO87/00434.

[30] Foreign Application Priority Data

Jul. 19, 1985 [DE] Germany ............... 35 26 362.8

[51] Int. Cl.⁶ ............... A61K 31/355; A61K 31/34; A61K 31/19
[52] U.S. Cl. ............... 514/469; 514/467; 514/572; 514/573
[58] Field of Search ............... 514/572, 573, 514/467, 469

[56] References Cited

U.S. PATENT DOCUMENTS

| | | | |
|---|---|---|---|
| 4,029,814 | 6/1977 | Bundy | 514/573 X |
| 4,048,328 | 9/1977 | Abraham et al. | 514/573 X |
| 4,263,207 | 4/1981 | Rokach et al. | 540/488 |
| 4,472,586 | 9/1984 | Hamel et al. | 514/826 X |
| 4,680,307 | 7/1987 | Muraoka et al. | 514/572 |

OTHER PUBLICATIONS

Potentiation of the Inhibitory Effect of a Thromboxane $A_2$ Antagonist (L–640,035) on Arterial Thrombosis Formation in Rabbit By The Angiotensin converting Enzyme Inhibitor Enalapril, Chi–Chung Chan and Anthony Ford–Hutchinson, European Journal of Pharmacology, 110 (1985) pp. 323–328.

International Dictionary of Medicine and Biology, vol. 1, John Wiley & Sons, 1986, p. 781, and vol. 11, p. 1296.

W. Witt et al., "Synergistic Antiplatelet and Antithrombotic Effects of a Prostacyclin Analogue (Iloprost) Combined with a Thromboxane Antagonist (Sulotroban) in Guinea Pigs and Rats", Thrombosis Research 51; 607–616 (1988).

S. Stuerzebecher et al., "The $PGI_2$–Analogue Iloprost and the $TXA_2$–Receptor Antagonist Sulotroban Synergistically Inhibit $TXA_2$–Dependent Platelet Activation", Prostaglandins, vol. 36, No. 6, pp. 751–760 (Dec. 1988).

*Primary Examiner*—Theodore J. Criares
*Attorney, Agent, or Firm*—Millen, White, Zelano & Branigan

[57] ABSTRACT

Combination products containing a prostaglandin (PG), prostacyclin (PC) or a prostacyclin analog (PCA) and a thromboxane receptor antagonist (TXAA) are suitable for joint application to thrombotic and thromboembolic syndromes.

20 Claims, No Drawings

PROSTACYCLINS, THEIR ANALOGS OR PROSTAGLANDINS AND THROMBOXANE ANTAGONISTS FOR TREATMENT OF THROMBOTIC AND THROMBOEMBOLIC SYNDROMES

This application is a continuation of application Ser. No. 07/041,013, filed Mar. 18, 1987, now abandoned.

The invention relates to a combination product for joint use in treating of thrombotic and thromboembolic syndromes with conditions of elevated intravascular platelet activity and thus of elevated tendency to platelet aggregation and platelet adhesion as also elevated blood clotting, containing a prostacyclin, a prostacyclin analog or a prostaglandin (PC/PCA/PG) and a thromboxane receptor antagonist (TXAA).

The invention also relates to the use of PC/PCA/PG in combination with a thromboxane receptor antagonist for application in: prophylaxis and therapy of coronary heart diseases, coronary thrombosis, myocardial infarct, peripheral arterial disease, diabetic vascular changes, arteriosclerosis and thrombosis, stroke, prophylaxis and therapy of ischemic attacks of the CNS, migraine, shock therapy, inhibition of bronchoconstriction, inhibition of gastric acid secretion; further possibilities of use of the combination are cytoprotection of the gastrointestinal mucous membrane, cytoprotection in the liver, kidney and pancreas, lowering of the pulmonary vascular resistance and of the pulmonary blood pressure, stimulation of renal circulation, application instead of heparin or as adjuvant in dialysis, hemofiltration, conservation of bank blood plasma, especially of banked blood platelets, inhibition of labor pains, treatment of toxemias of pregnancy, elevation of the cerebral circulation, etc.; in addition, the combination product can be used as an antiallergic agent and as an antiproliferative agent.

The combination can also, e.g., be applied jointly with calcium antagonists, thromboxane synthetase inhibitors, typical anticoagulants such as heparin, coumarin or aspirin and corresponding active substances, with phosphodiesterase inhibitors, with angiotensin converting enzyme (ACE) inhibitors, with vasodilating active substances, especially with beta receptor blockers, antiphlogistic agents, antipyretic agents and antiallergic agents etc.

It is already known that for treating acute and chronic thrombotic and thromboembolic diseases prostaglandin $E_1$, prostacyclin and prostacyclin analogs are used [information for use for Prostavasin($^R$) of the Sanol Schwarz GmbH; Moncada. S., Br. J. Pharmacol. 76/1, 3–31 (1982); Schillinger, E., T. Krais, G. Stock, New Drug Annual: Cardiovascular Drugs, Raven Press, in printing].

Besides the advantages of these forms of treatment, which consist in a strong inhibition of all stimulants of platelet aggregation, these therapies are limited by the cardiovascular side effects, especially the pronounced lowering of blood pressure.

No satisfactory proof of effect for this therapy principle has been produced for TXAA in clinical research up to now.

Arriving at better principles effective in regard to anti-aggregation by raising of the plasma level of the endogenous prostacyclin in combination with a TXAA [Chan, C-C., A. Ford-Hutchinson, Europ. J. of Pharmcol. 110, 323–328, (1985)] is to be considered as insufficient, especially since a dosibility and in general a reliable and reproducible increase of the endogenous prostacyclin is not possible. Moreover, with endogenous prostacyclin there is no possibility, as in the application of synthetic PC/PCA/PG, of separating the effects of prostacyclin from side effects.

It has now been found in a surprising way that the side effects typical for PC/PCA/PG and the insufficient effectiveness of TXAA can be avoided or compensated for if PC/PCA/PG and TXAA are used jointly in the treatment of the above-mentioned syndromes. While the platelet-inhibiting antithrombotic and antithrombogenic effect of both classes of active substances is mutually potentiated, there is achieved a reduction of the cardiovascular side effects of PC/PCA/PG as a result of the reduction of amounts of the individual active substances possible with the combination.

This invention provides a combination product for joint application in thrombotic and thromboembolic syndromes, containing prostacyclin, a prostacyclin analog or a prostaglandin and a thromboxane receptor antagonist. Aspects includes those where the PC/PCA/PG and TXAA are in a weight ratio of 1:1 to 1:10000; wherein the PC/PCA/PG and TXAA are present in separate dose units; wherein the PC/PCA/PG and TXAA are present together in one dose unit; wherein the PC/PCA/PG dose unit contains 25–250 micrograms of Iloprost or a biologically equivalent amount of another PC/PCA/PG; and wherein a TXAA dose unit contains 50–1000 mg of BM 13 177 or a biologically equivalent amount of another TXAA. Consequently the therapeutic range of the individual active substances is increased.

Amounts by weight of prostacyclin/prostacyclin analog/prostaglandin and thromboxane receptor antagonist can be used which are greatly reduced with the joint application in comparison with the necessary dosages of the individual active substances used up to now.

PC/PCA/PG and TXAA are combined in a dose unit or used separately and simultaneously or sequentially in a weight ratio of essentially about 1:1 to 1:10000 (e.g., in the same vehicle, a tablet or also an oily solution such as a benzylbenzoate/castor oil mixture).

The sequential treatment is of particular importance inasmuch as with such treatments, in which a decrease of the PC/PCA/PG effect occurs or is to be expected (tachyphylaxis, [Sinzinger, H., S. Reiter, Prostagl. Leukotr. and Medicine 13/3, 281–288 (1984)]), by alternately gradually increasing and decreasing therapy with PC/PCA/PG and TXAA such a reduction of effect can be prevented.

Suitable compounds of the prostacyclin/prostacyclin analog/prostaglandin series for use according to the invention are all substances which exhibit properties of inhibiting of blood platelet aggregation and are described, for example, in:

R. C. Nickolson, M. H. Town and H. Vorbrueggen, Med. Res. Rev. 5 (1985), B. I. R. Whittle and S. Moncada, Progress in Medicinal Chemistry 21, 236 (1984), P. A. Aristoff in Advances in Prostaglandin, Thromboxane and Leukotriene Research Vol. 14, 1985, p. 309, B. Raduechel and H. Vorbrueggen in Advances in Prostaglandin,, Thromboxane and Leukotriene Research Vol. 14, 1985, p. 263, in European patent applications of publication numbers 0011591, 0055208, 0069692, 0086404, 0099538, 0119949 as well as in DE-OS 34 08 699 and DE-OS 35 10 978.

For example, there can be named:

Prostacyclin $PGI_2$, 15-cyclopentyl-omega-pentanor-5(E)-carbacylic (ONO-41 483; Prost. and Med. 10, 53, (1983), 5-{(E)-(1S,5S,7R)-7-hydroxy-6-[(3S,4S)-3-hydroxy-4-methyl-nona-1,6-diinyl]-bicyclo[3.3.0]-octan-3-ylidene}pentanoic acid (EP 0086404), (5E)-(16S)-13,14-didehydro-16,20-dimethyl-18,18–19,19-tetradehydro-2,3,4-trinor-1,5 inter-m-phenylene-6a-carbaprostaglandin $I_2$ (DE-OS 3408699), 5-{(E)-1S,5S,6R,7R)-7-hydroxy-6-[(3S,4RS)-3-hydroxy-4-methyl-1-octen-6-inyl]-bicyclo[3.3.0]-octan-3-ylidene}pentanoic acid (Iloprost, EP 0011591),
7-{(E)-(1S,5S,6S,7R)-7-hydroxy-6-[(3S,4S)-3-hydroxy-4-methyl-nona-1,6-diinyl]bicyclo[3.3.0]-octan-3-ylidene}-5-oxa-heptanoic acid (EP 0099538),
(5Z,13E,9alpha,11alpha,15S)-2,3,4-trinor-inter-m-phenylene-6,9-epoxy-11,15-dihydroxy-15-cyclohexyl-16,17,18,19,20-pentanor]-prostadiene acid (C G 4305, Arzn. Forsch. 1983, 1240) as well as the corresponding sodium salt (C G 4203, Drugs Future 9, 494, (1984).
beta-thia-imino-prostacyclin (Hoe 892, Prost. and Med. 10, 231 (1983)),
9-methyl-carbacylin (J. Org. Chem. 48, 534 (1983)),
5-{(E)-(1S,5S,6S,7R)-7-hydroxy-6-[(3S,4S)-3-hydroxy-4-methyl-nona-1,6-diinyl]-bicyclo[3.3.0]-octan-3-ylidene}-3-oxa-pentanoic acid (EP 0119949),
5-{(Z)-(1S,5S,6S,7R)-7-hydroxy-6-[(3S,4S)-3-hydroxy-4-methyl-nona-1,6-diinyl]-bicyclo[3.3.0]-octan-3-ylidene}-3-oxa-5-fluoropentanoic acid (EP 0099538),
7-oxo-16-methyl-18,19-didehydro-PGI$_2$ (DE-OS 3 035 454),
7-oxo-PGI$_2$ (DE-OS 3 035 454),
Prostaglandin E$_1$,
6-keto-prostaglandin E$_1$,
(5Z,13E)-(9R,11R,15S)-9-chloro-15-cyclohexyl-11,15-dihydroxy-16,17,18,19–20-pentanor-5,13-prostadiene acid (DE-OS 3, 510 978),
17S,20-dimethyl-trans-2,3-didehydro-PGE$_1$ (ONO 1206, Drugs Future 7, 116 (1982).

Instead of the indicated prostanoic acids, their physiologically compatible salts with inorganic or organic bases, as, for example, sodium hydroxide, potassium hydroxide, tris-(hydroxymethyl)-aminomethane, glucamine, N-methylglucamine, morpholine, lysine, arginine can be used.

As thromboxane receptor antagonists are suitable all compounds which have a sufficient affinity for the thromboxane receptor and have no or only insignificant thromboxane antagonistic activity in the dose range used, such as, e.g., described in: J 5 5017–315; U.S. Pat. No. 4,472,586; U.S. Pat. No. 4,263,207; U.S. Pat. No. 4,394,515; U.S. Pat. No. 4,282,365; BE-883-713; J5 7093-962; J6 0004-154-A; EP--43-292; EP--82-646-A; DE-3346-047-A; WO 8400-754-A; U.S. Pat. No. 4,474,804; DE 3401-986-A; DE 3127-343; BE-897-763-A; EP--74-861; AU 8425-607-A; EP--78-668; DE 3339- 019-A; EP-137-426-A and in N. H. Wilson and R. L. Jones in: Advances in Prostaglandin, Thromboxane and Leukotriene Research 14, 420–423 (1985), as well as K. Stegmeier et al. in: Thrombosis Research 35, 379–395 (1984).

There can be mentioned, for example:
4-[2-(benzenesulfonamido)-ethyl]-phenoxyacetic acid (BM 13 177) [K. Stegmeier et al. in: Thrombosis Research 35, 379–395, 1984].
[1alpha(Z), 2beta,5alpha]-(±)-7-[5-[[(1,1-biphenyl)-4-yl] methoxy]-2-(4-morpholinyl)-3-oxocyclopentyl]-4-heptanoic acid (AH 23848) (Br. J. Pharmac. (1985), 86, 259).
[1beta,2alpha(5Z),3alpha,4beta]-7-[[2-[phenylamino)carbonyl]hydrazino]methyl]-7-oxabicyclo[2.2.1]hept-2-yl]-5-heptenoic acid (SQ 29.548) (Prostaglandins 29, 785 (1985))
4-(4-chlorobenzenesulfonylamino)-ethyl-benzene acetic acid (BM 13 505) (Intern. Conf. Leukotrienes and Prostanoids in Health and Disease, Tel-Aviv, October 1985, p. 10)
7-[3-[[[(phenylamino)carbonyl]hydrazonol]methyl]bicyclo [2.2.1]hept-2-yl]-,[1alpha, 2beta, (Z), 3alpha, 4alpha] (EP 045) and
7-{(1S,2S,3S,4R)-3-[1-(3-[phenylthioureidoimino)ethyl]-bicyclo[2.2.1]heptane-2-yl}-5-heptenoic acid (EP 092) [both substances R. A. Armstrong et al. in Br. J. Pharmacol. 84, 595–607, 1985].
Dibenzo[b,f]thiepin-3-methanol,5,5-dioxide (L 640035) [C-C. Chan in: Europ. J. Pharmacol. 110 (3), 323–328, 1985].
2,7-(1H)-isoquinolinedisulfonamide, N7-(3-chlorophenyl)-N2-[[7-[[(3-chlorophenyl)amino]sulfonyl]-3,4-dihydro-2(1H)-isoquinolinal]sulfonyl]-3,4-dihydro (SKF 88046) [B. M. Wiechman et al. in: Prostaglandins Leukotrienes and Medicine 15, 167–175, 1984].

The PC/PCA/PG are used in amounts that clearly are below the amounts otherwise used for inhibition of intravascular platelet aggregation. With Iloprost used as the PCA, it is possible according to the invention generally to manage with 10–1000 micrograms, preferably with 50–250 micrograms per day. The application can take place, for example, enterally or parenterally, by inhalation or also transdermally or locally.

In the case of intravenous infusion of Iloprost, amounts, for example, of about 50–150 micrograms per day are necessary.

In the case of oral application, 125–250 micrograms per day is used.

A dose unit of Iloprost contains about 100 micrograms/ml as primary solution for diluting to the usual infusion carrier solutions for intravenous application.

For oral use, a dose unit contains 25–50 micrograms, in case of slow-release formulations 25–250 micrograms, as tablet, dragee, capsule, pill, suspension or solution, which can be produced in the usual way with the additives and carrier substances customary in galenics. For local, topical or transdermal application, for example, systems such as patches or suppositories are suitable.

Also according to the invention biologically equivalent amounts of other prostacyclin analogs or prostaglandins can be used.

The thromboxane receptor antagonists according to the present invention are used in amounts that generally are below the amounts used so far in human studies [Riess, H., E. Hiller, B. Reinhardt, C. Braeuning in: Thrombosis Research 35, 371–378, 1984]. In general 100–2000 mg/day, preferably 200–800 mg/day of BM 13 177 or 1–100 mg/day, preferably 2–50 mg/day, of AH23848 or SQ 29548 or a biologically equivalent amount of another thromboxane receptor antagonist suffices.

The TXAA can be applied, for example, enterally or parenterally, by inhalation or also transdermally or locally.

For the preferred oral application especially tablets, dragees, capsules, pills, suspensions or solutions are suitable, which can be produced in the usual way with the additives and carrier substances customary in galenics.

For local application, transdermal systems, for example, such as patches are used.

A dose unit for oral or parenteral application contains about 50–300 mg, as slow-release formulation 100–1000 mg, of BM 13 177/day or a biologically equivalent amount of another thromboxane receptor antagonist.

The joint treatment with PCA and TXAA takes place, depending on whether an acute, subacute or a chronic pathological process is involved, over a few days to weeks and months, in which PCA and TXAA are administered in a dose unit separately and simultaneously or sequentially.

The following examples are to explain the galenic formulation:

EXAMPLE 1

Composition of a Combination Tablet

|   | % | Amount/tablet [mg] |
|---|---|---|
| 1. Iloprost (as sol. in 50% ethanol) | 0.01 | 0.05 |
| 2. BM 13 177 | 50.0 | 250.0 |
| 3. Lactose | 34.99 | 174.95 |
| 4. Corn starch | 10.0 | 50.0 |
| 5. Polyvinylpyrrolidone 2500 | 3.0 | 15.0 |
| 6. Stearic acid | 2.0 | 10.0 |
|   | 100% | 500.00 mg |

Components 3, 4 and 5 are sifted, mixed and granulated with the solution of 1. After drying, 2 and 6 are mixed in after the other and the molding compound is molded into round tablets with an 11-mm diameter.

EXAMPLE 2

Composition of a Combination Tablet

|   | % | Amount/tablet [mg] |
|---|---|---|
| 1. Iloprost (as sol. in 50% ethanol) | 0.02 | 0.05 |
| 2. SQ 29 458 | 4.0 | 10.0 |
| 3. Lactose | 65.98 | 164.95 |
| 4. Corn starch | 20.0 | 50.0 |
| 5. Polyvinylpyrrolidone 2500 | 6.0 | 15.0 |
| 6. Stearic acid | 4.0 | 10.0 |
|   | 100% | 250.00 mg |

Components 3, 4 and 5 are sifted, mixed and granulated with the solution of 1. After drying, 2 and 6 are mixed in one after the other and the molding compound is molded into round tablets with an 11-mm diameter.

EXAMPLE 3

Composition of a Combination Tablet

|   | % | Amount/tablet [mg] |
|---|---|---|
| 1. Iloprost (as sol. in 50% ethanol) | 0.02 | 0.05 |
| 2. AH 23 848 | 1.0 | 2.5 |
| 3. Lactose | 68.98 | 172.45 |
| 4. Corn starch | 20.0 | 50.0 |
| 5. Polyvinylpyrrolidone 2500 | 6.0 | 15.0 |
| 6. Stearic acid | 4.0 | 10.0 |
|   | 100 | 250.00 mg |

Components 3, 4 and 5 are sifted, mixed and granulated with the solution of 1. After drying, 2 and 6 are mixed in one after the other and the molding compound is molded into round tablets with an 11-mm diameter.

EXAMPLE 4

Composition of a Combination Tablet

|   | % | Amount/tablet [mg] |
|---|---|---|
| 1. Iloprost Na salt (dissolved in dist. water) | 0.0104 | 0.052 ($\hat{=}$ 0.05 mg Iloprost) |
| 2. BM 13 177 | 50.0 | 250.0 |
| 3. Lactose | 34.99 | 174.95 |
| 4. Corn starch | 10.0 | 50.0 |
| 5. Polyvinylpyrrolidone 2500 | 3.0 | 15.0 |
| 6. Stearic acid | 2.0 | 10.0 |
|   | 100% | 500.00 mg |

Components 3, 4 and 5 are sifted, mixed and granulated with the solution of 1. After drying, 2 and 6 are mixed in one after the other and the molding compound is molded into round tablets with an 11-mm diameter.

EXAMPLE 5

Composition of a Combination Tablet

|   | % | Amount/tablet [mg] |
|---|---|---|
| 1. Iloprost (as inclusion compound) with alpha, beta or gamma cyclodextrin, 3% (g/g) | 0.33 | 1.66 ($\hat{=}$ 0.05 mg Iloprost) |
| 2. BM 13 177 | 50.0 | 250.0 |
| 3. Microcrystalline cellulose | 35.67 | 178.34 |
| 4. Corn starch | 12.0 | 60.0 |
| 5. Stearic acid | 2.0 | 10.0 |
|   | 100% | 500.00 mg |

The formulation components, with the exception of stearic acid, are sifted and mixed for 15 minutes. Stearic acid (sifted) is added and mixed for 3 more minutes with the other formulation components. The molding compound is molded into round tablets with an 11-mm diameter.

PHARMACOLOGICAL OBSERVATIONS

1. Thrombocyte Function In Vitro (Human PRP)

BM 13 177 (in the text, BM) and Iloprost are tested in their action on thrombocyte aggregation and thrombocyte shape change against stimulants U 46 619 (9,11-dideoxy, 9alpha-11alpha-methanoepoxy $PGF_{2alpha}$, stable $TXA_2$ agonist) and ADP and the $IC_{50}$ values are determined. Then in several independent tests the action of a combination of the two substances on the aggregation (U 46 619 and ADP) in various concentrations is tested; especially the combination of low dosages and of dosages of the two substances in the range of the $IC_{50}$ values is tested.

Methodology

Platelet aggregation and shape change are measured as light-optical phenomena in stimulated PRP (platelet rich plasma) samples. In this case, the shape change is detected as the density increase of the sample by transition of the discoid rest shape of the platelet into a spherozytic shape with formation of pseudopodlike membrane formations and represented on a recorder. The aggregation is photometrically detected as density increase by clumping and "precipitation" of platelet aggregates and represented on a recorder.

Results

Iloprost, depending on the concentration, inhibits the platelet aggregation induced by U 46 619 and the shape change. The $IC_{50}$ for the aggregation inhibition is 1.3–2.6 nm, for the shape change inhibition the $IC_{50}$ is 0.52–1.3 nM.

The 2nd wave of the aggregation induced by ADP is inhibited with an $IC_{50}$ of 0.26–0.65 nM depending on the concentration.

BM 13 177, depending on the concentration, inhibits the platelet aggregation induced by U 46 619 and the shape change. The $IC_{50}$ is 1.65–6.6 microM for the aggregation, 1.65–3.3 microM for the shape change.

The 2nd wave of the aggregation induced by ADP is inhibited with an $IC_{50}$ of 0.33–0.66 microM depending on the concentration.

Combination of thromboxane receptor antagonist and Iloprost

In the combination of BM 13 177 with Iloprost the platelet aggregation induced by U 46 619 and platelet shape change and the 2nd wave of aggregation induced by ADP are strongly inhibited in the case of concentrations of both active substance which are on the threshold or below the threshold area. The inhibition effects of both active substances are thus potentiated (see table).

Tables

Example 1: Aggregation by 100 ng/ml U 46 619

| Active substance | Concentration | % Inhibition |
| --- | --- | --- |
| 1 BM 13 177 | 0.66 microM | 16% |
| 2 Iloprost | 0.1 ng/ml | 2% |
| 1 + 2 | | 65% |

Example 2: Shape change by 50 ng/ml U 46 619

| Active substance | Concentration | % Inhibition |
| --- | --- | --- |
| 1 BM 13 177 | 0.66 microM | 28% |
| 2 Iloprost | 0.1 ng/ml | no inhibition |
| 1 + 2 | | 61% |

Example 3: 2nd wave of aggregation by $0.5 \times 10^{-6}$ M ADP

| Active substance | Concentration | % Inhibition |
| --- | --- | --- |
| 1 BM 13 177 | 0.165 microM | no inhibition |
| 2 Iloprost | 0.1 ng/ml | no inhibition |
| 1 + 2 | | 60% |

2. Intravascular Thrombocyte Aggregation on Anesthetized Rats

Methodology

The influence of the intravascular thrombocyte aggregation is examined on urethane anesthetized rats.

Collagen (100 micrograms/kg i.v. bolus) causes transitory thrombocytopenias (a transient loss of blood platelet concentration), measured by continuous taking of blood from the A. carotis (50 microliter/min) and thrombocyte counting in the Technicon Autocounter. The change of the collagen-induced thrombocytopenia (% of loss) in comparison with the initial value (=2nd collagen injection) serves as a measurement for the inhibition of the intravascular platelet aggregation.

Results

Iloprost (0.1–0.33–1.0 micrograms/kg/min) inhibits the collagen-induced thrombocytopenia, depending on the dose. BM 13 177 inhibits thrombocytopenia in lowest dosage (0.5 mg/kg/min) by about 27±6% (MW±SE), an effect which cannot be increased by raising the dosage (1.0–2.0 mg/kg/min). The combination of a threshold dose of Iloprost (0.1 microgram/kg/min) with the lowest tested dose of BM 13 177 (0.5 mg/kg/min) produces a significantly (alpha=0.05; Lord test) stronger inhibition of 45±2% with respect to the individual doses.

3. Mesenteric Arteriole Thrombosis on Anesthetized Guinea Pigs

Methodology

A mesenteric loop for vital microscopy is prepared on anesthetized guinea pigs. After electrical lesion of an arteriole, under controlled conditions and after substance application, ADP is applied topically until finding of a thrombogenic dose (occlusion by platelet thrombus).

Parameters: increasing of the thrombogenic ADP concentration vs. initial value; i.v. infusion of Iloprost, i.v. injection of BM 13 177.

Results

BM 13 177 (25 mg/kg i.v.) significantly increases by about a factor of 4 the ADP concentration necessary for dissolving occluding platelet thrombi on electrically previously damaged mesenteric arterioles of anesthetized guinea pigs. Iloprost increases the thrombogenic ADP concentration by a factor of 2.8 in the threshold dose of 0.1 microgram/kg/min i.v.

The combination of BM 13 177 (25 mg/kg i.v.), followed by i.v. infusion of Iloprost (0.1 microgram/kg/min) increases the thrombogenic ADP concentration by a factor of 12.

On a test model for the arterial platelet-induced thrombosis, the combination of the $TXA_2$ antagonist BM 13 177 and of the prostacyclin analog Iloprost results in a potentiated antithrombogenetic effect.

4. Jugular Vein Thrombosis on Anesthetized Rats

Methodology

By stressing of the jugular vein of rats anesthetized with urethane with a metal punch cooled to −15° C. (200 g, 2 min) the vessel is predamaged. The thrombus grown within 3 hours on this site is quantified (Hb content wet weight) by determinations of its Hb content (difference damaged-undamaged vessel segment).

The infusion of the test substances begins 15 min before damaging the vein and is continued until the end of the test.

Results

The infusion of Iloprost, in a dosage (30 ng/kg/min, i.v.) that is not significantly effective as individual dose in combination with a dose of BM 13 177 (20 mg/kg, i.v. bolus+50 micrograms/kg/min, i.v.) also ineffective as monotherapy, produces a significant reduction of the Hb content of the thrombi to values of undamged controls.

BM 13 177 as monotherapy is not antithrombotically effective on the jugular vein thromboisis model of the rats. The combination with a dose of Iloprost hemodynamically ineffective in regard to antiaggregation, completely suppresses the thrombus growth.

5. Blood Pressure of Spontaneously Hypertonic (SH) Rats

Methodology

On awake SH rats, in which a venous catheter for substance application and an arterial catheter for blood pressure measurements is implanted, the behavior of the blood pressure and heart frequency under infusion of test substances are observed. Iloprost is infused jointly for 20 minutes in a threshold dose of 0.3 microgram/kg/min (20% reduction of diastolic blood pressure) with a high dose of BM 13 177, 2 mg/kg/min (see platelet inhibition in vivo, 27% inhibition at 2 mg/kg i.v. infusion) (n=6 animals).

Results

The hemodynamical changes, blood pressure drop and increase of heart frequency caused by Iloprost are insignificantly influenced by BM 13 177.

While the maximum blood pressure reduction under Iloprost is not influenced by BM 13 177, the effect after the end of the infusion more quickly subsides under the combination treatment.

A reinforcement of the blood pressure reduction effect of Iloprost by BM 13 177 must not be expected even with high dosages of BM 13 177.

We claim:

1. A composition comprising amounts, in total, effective for inhibiting platelet aggregation or adhesion of (a) prostacyclin, a prostacyclin analog or a prostaglandin (PC/PGA/PG) and (b) a thromboxane receptor antagonist (TXAA), with the proviso that said thromboxane $A_2$ receptor antagonist is not also a thromboxane $A_2$ synthetase inhibitor.

2. A composition according to claim 1, where the PC/PCA/PG and TXAA are in a weight ratio of 1:1 to 1:10000.

3. A composition according to claim 1, wherein the PC/PCA/PG and TXAA are present in separate dose units.

4. A composition according to claim 1, wherein the PC/PCA/PG and TXAA are present together in one dose unit.

5. A composition according to claim 1, wherein a PC/PCA/PG dose unit contains 25–250 micrograms of Iloprost; 5-{(E)-(1S,5S,6R,7R)-7-hydroxy-6-[(E)-(3S,4RS)-3-hydroxy-4-methyl-5-octen-6-inyl]-bicyclo[3.3.0]-octan-3-ylidene} pentanoic acid or a biologically equivalent amount of another PC/PCA/PG.

6. A composition according to claim 1, wherein a TXAA dose unit contains 50–1000 mg of BM 13 177.

7. A pharmaceutical formulation comprising separate dose units of (a) prostacyclin, a prostacyclin analog or a prostaglandin and (b) a thromboxane receptor antagonist, the total amounts thereof being effective for inhibiting platelet aggregation or adhesion, with the proviso that said thromboxane $A_2$ receptor antagonist is not also a thromboxane $A_2$ synthetase inhibitor.

8. A method for treating a thrombotic or thromboembolic syndrome comprising administering to a patient in need of such treatment a composition of claim 1.

9. A method of claim 8, wherein the PC/PCA/PG and TXAA are in a weight ratio of 1:1 to 1:10000.

10. A method of claim 8, where there are administered 25–250 micrograms of Iloprost as PC/PCA/PG or a biologically equivalent amount of another PC/PCA/PG.

11. A method of claim 8, where there are administered 50–1000 mg of BM 13 177 as TXAA or a biologically equivalent amount of another TXAA.

12. A method of claim 8, wherein the administration of PC/PCA/PG and TXAA is simultaneous.

13. A method of claim 8, wherein the administration of PC/PCA/PG and TXAA is sequential.

14. A method of claim 8, wherein the PC/PCA/PG and TXAA are present in the same dosage unit.

15. A method of claim 8, wherein the PC/PCA/PG and TXAA are administered in separate dosage units.

16. A method of reducing platelet aggregation or platelet adhesion in a patient during blood dialysis comprising treating the blood of the patient with a composition of claim 1.

17. A method of reducing platelet aggregation or platelet adhesion in a patient during hemofiltration comprising treating the blood of the patient with a composition of claim 1.

18. A method preventing or reducing platelet loss during extracorporeal circulation, in a mammalian species, which comprises administering to a mammalian species in need of such treatment an effective amount of thromboxane $A_2$ receptor antagonist with prostacyclin and/or a prostacyclin mimic, with the proviso that said thromboxane $A_2$ receptor antagonist is not also a thromboxane $A_2$ synthetase inhibitor.

19. A method of claim 18, wherein the thromboxane $A_2$ receptor antagonist is administered with prostacyclin and/or a prostacyclin mimic.

20. A method of claim 19, wherein the thromboxane $A_2$ receptor antagonist is [1β,2α(5Z),3α,4β]-7-[[2-[(phenylamino)carbonyl]hydrazino]methyl]-7-oxabicyclo[2.2.1]-hept-2-yl]-5-heptenoic acid.

* * * * *